US008663316B2

(12) United States Patent
Elliott

(10) Patent No.: US 8,663,316 B2
(45) Date of Patent: Mar. 4, 2014

(54) ENDOLUMINAL DEVICE HAVING ENHANCED AFFIXATION CHARACTERISTICS

(75) Inventor: Christopher J. Elliott, Hopkinton, MA (US)

(73) Assignee: Lifeshield Sciences, LLC, Plano, TX (US)

( * ) Notice: Subject to any disclaimer, the term of this patent is extended or adjusted under 35 U.S.C. 154(b) by 99 days.

(21) Appl. No.: 11/318,736

(22) Filed: Dec. 27, 2005

(65) Prior Publication Data
US 2006/0100684 A1    May 11, 2006

Related U.S. Application Data

(63) Continuation of application No. 10/374,854, filed on Feb. 26, 2003, now Pat. No. 7,025,779.

(51) Int. Cl.
*A61F 2/06* (2013.01)
(52) U.S. Cl.
USPC ........................................................ 623/1.35
(58) Field of Classification Search
USPC ............................................. 623/1.11–1.54
See application file for complete search history.

(56) References Cited

U.S. PATENT DOCUMENTS

| 4,286,341 A | 9/1981 | Greer et al. |
| 4,313,231 A | 2/1982 | Koyamada |
| 4,355,426 A | 10/1982 | MacGregor |
| 4,562,596 A | 1/1986 | Kornberg |
| 4,617,932 A | 10/1986 | Kornberg |
| 5,035,706 A * | 7/1991 | Giantureo et al. ............ 606/198 |
| 5,064,435 A * | 11/1991 | Porter .......................... 623/23.7 |
| 5,151,105 A | 9/1992 | Kwan-Gett |
| 5,282,824 A * | 2/1994 | Gianturco .................... 623/1.13 |
| 5,316,023 A | 5/1994 | Palmaz et al. |
| 5,330,500 A | 7/1994 | Song |
| 5,354,308 A * | 10/1994 | Simon et al. ................. 623/1.15 |

(Continued)

FOREIGN PATENT DOCUMENTS

| JP | 4-231954 | 8/1992 |
| JP | 2003-000622 | 1/2003 |

(Continued)

OTHER PUBLICATIONS

International Search Report for corresponding International Application PCT/US2004/003812 dated Jun. 22, 2004.

(Continued)

*Primary Examiner* — David Isabella
*Assistant Examiner* — Ann Schillinger
(74) *Attorney, Agent, or Firm* — Brooks, Cameron & Huebsch, PLLC

(57) ABSTRACT

An endoluminal device for affixation to a wall of a body lumen having a neck region defined by a relatively narrow width and a shoulder region that diverges from the neck region to a relatively wider width. The device comprises a bulbous portion having a shoulder portion with a diameter profile that conforms to the shoulder region of the lumen, and a converging diameter portion sized not to conform to the body lumen diameter profile. In some embodiments, a plurality of affixation members in an area of the device that typically extends from a distal end of the device through the shoulder portion. In one embodiment, the device comprises an endograft for repair of an aneurysm, such as an abdominal aortic aneurysm (AAA).

29 Claims, 3 Drawing Sheets

(56) References Cited

U.S. PATENT DOCUMENTS

| | | | | |
|---|---|---|---|---|
| 5,360,443 | A | 11/1994 | Barone et al. | |
| 5,366,504 | A * | 11/1994 | Andersen et al. | 623/1.5 |
| 5,387,235 | A * | 2/1995 | Chuter | 623/1.11 |
| 5,522,880 | A | 6/1996 | Barone et al. | |
| 5,540,712 | A * | 7/1996 | Kleshinski et al. | 623/1.19 |
| 5,562,728 | A * | 10/1996 | Lazarus et al. | 623/1.14 |
| 5,571,171 | A | 11/1996 | Barone et al. | |
| 5,575,817 | A | 11/1996 | Martin | |
| 5,578,071 | A | 11/1996 | Parodi | |
| 5,578,072 | A | 11/1996 | Barone et al. | |
| 5,591,228 | A * | 1/1997 | Edoga | 128/898 |
| 5,609,627 | A | 3/1997 | Goicoechea et al. | |
| 5,665,117 | A | 9/1997 | Rhodes | |
| 5,683,452 | A | 11/1997 | Barone et al. | |
| 5,693,087 | A | 12/1997 | Parodi | |
| 5,693,088 | A | 12/1997 | Lazarus | |
| 5,716,393 | A | 2/1998 | Lindenberg et al. | |
| 5,733,325 | A | 3/1998 | Robinson et al. | |
| 5,782,904 | A | 7/1998 | White et al. | |
| 5,843,164 | A * | 12/1998 | Frantzen et al. | 623/1.16 |
| 5,935,161 | A | 8/1999 | Robinson et al. | |
| 5,968,053 | A | 10/1999 | Revelas | |
| 6,004,347 | A * | 12/1999 | McNamara et al. | 623/23.64 |
| 6,030,415 | A | 2/2000 | Chuter | |
| 6,039,749 | A | 3/2000 | Marin et al. | |
| 6,077,296 | A | 6/2000 | Shokoohi et al. | |
| 6,077,297 | A * | 6/2000 | Robinson et al. | 623/1.11 |
| 6,102,940 | A | 8/2000 | Robichon et al. | |
| 6,152,956 | A | 11/2000 | Pierce | |
| 6,156,064 | A * | 12/2000 | Chouinard | 623/1.44 |
| 6,162,244 | A | 12/2000 | Braun et al. | |
| 6,162,246 | A | 12/2000 | Barone | |
| 6,168,610 | B1 | 1/2001 | Marin et al. | |
| 6,168,619 | B1 * | 1/2001 | Dinh et al. | 623/1.13 |
| 6,187,036 | B1 | 2/2001 | Shaollan et al. | |
| 6,197,049 | B1 | 3/2001 | Shaolian et al. | |
| 6,214,036 | B1 | 4/2001 | Letendre et al. | |
| 6,241,759 | B1 | 6/2001 | Piplani et al. | |
| 6,258,121 | B1 | 7/2001 | Yang et al. | |
| 6,267,783 | B1 | 7/2001 | Letendre et al. | |
| 6,270,524 | B1 | 8/2001 | Kim | |
| 6,273,909 | B1 | 8/2001 | Kugler et al. | |
| 6,280,467 | B1 | 8/2001 | Leonhardt | |
| 6,287,335 | B1 | 9/2001 | Drasler et al. | |
| 6,290,731 | B1 | 9/2001 | Solovay et al. | |
| 6,306,164 | B1 | 10/2001 | Kujawski | |
| 6,312,462 | B1 | 11/2001 | McDermott et al. | |
| 6,331,190 | B1 * | 12/2001 | Shokoohi et al. | 623/1.22 |
| 6,331,191 | B1 * | 12/2001 | Chobotov | 623/1.44 |
| 6,358,556 | B1 | 3/2002 | Ding et al. | |
| 6,364,856 | B1 | 4/2002 | Ding et al. | |
| 6,508,835 | B1 | 1/2003 | Shaolian et al. | |
| 6,582,458 | B1 | 6/2003 | White et al. | |
| 6,585,758 | B1 | 7/2003 | Chouinard et al. | |
| 6,592,615 | B1 * | 7/2003 | Marcade et al. | 623/1.16 |
| 6,602,280 | B2 * | 8/2003 | Chobotov | 623/1.11 |
| 6,610,087 | B1 | 8/2003 | Zarbatany et al. | |
| 6,693,086 | B1 | 2/2004 | Dow et al. | |
| 6,890,350 | B1 | 5/2005 | Walak | |
| 7,025,779 | B2 * | 4/2006 | Elliott | 623/1.35 |
| 2003/0163188 | A1 | 8/2003 | Haverkost et al. | |
| 2003/0216802 | A1 * | 11/2003 | Chobotov | 623/1.13 |
| 2003/0220683 | A1 | 11/2003 | Minasian et al. | |
| 2004/0117002 | A1 * | 6/2004 | Girton et al. | 623/1.16 |
| 2004/0117003 | A1 * | 6/2004 | Ouriel et al. | 623/1.35 |
| 2005/0060023 | A1 * | 3/2005 | Mitchell et al. | 623/1.15 |

FOREIGN PATENT DOCUMENTS

| | | | |
|---|---|---|---|
| WO | 92/19310 | 11/1992 | |
| WO | 95/32757 | 12/1995 | |
| WO | 97/36556 | 10/1997 | |
| WO | WO 01/08600 A2 * | 2/2001 | A61F 2/06 |
| WO | WO 01/72239 | 10/2001 | |
| WO | WO 02/36045 | 5/2002 | |
| WO | 02/087473 | 11/2002 | |

OTHER PUBLICATIONS

Japanese Office Action in related Japanese Patent Application No. 2006-503443. Jan. 12, 2010. 7 pgs.

Japanese Office Action in related Japanese Patent Application No. 2006-503443 dated Sep. 30, 2010. 95 pgs.

Japanese National Phase PCT Laid-Open Publication No. 10-504200 (no English Abstract available) (corresponding to WO 95/32757), Apr. 21, 1995.

Japanese National Phase PCT Laid-Open Publication No. 06-507096 (no English Abstract available) (corresponding to WO 92/19310), Apr. 24, 1992.

Japanese Registered Utility Model Publication No. 3009638 (no English Language counterpart).

Japanese National Phase PCT Laid-Open Publication No. 2001-502192 (no English Abstract available) (corresponding to WO 97/36556 with English Abstract), Mar. 27, 1997.

Canadian Office Action in related Canadian Patent Application No. 2,526,848. Jul. 7, 2010. 3 pgs.

Japanese Office Action in related Japanese Patent Application No. 2006-503443. Mar. 25, 2011. 69 pgs.

* cited by examiner

ENDOLUMINAL DEVICE HAVING ENHANCED AFFIXATION CHARACTERISTICS

This application is a continuation application of U.S. patent application Ser. No. 10/374,854, filed on Feb. 26, 2003, now U.S. Pat. No. 7,025,779.

FIELD OF THE INVENTION

This invention relates generally to endoluminal devices, particularly stents and grafts for placement in an area of a body lumen that has been weakened by damage or disease, such as an aneurysm of the abdominal aorta, and more particularly to devices having characteristics that enhance affixation of the devices to the body lumen.

BACKGROUND OF THE INVENTION

Medical devices for placement in a human or other animal body are well known in the art. One class of medical devices comprises endoluminal devices such as stents, stent-grafts, filters, coils, occlusion baskets, valves, and the like. A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. A covered stent is commonly referred to in the art as an intraluminal prosthesis, an endoluminal or endovascular graft (EVG), a stent-graft, or endograft.

An endograft may be used, for example, to treat a vascular aneurysm by removing the pressure on a weakened part of an artery so as to reduce the risk of rupture. Typically, an endograft is implanted in a blood vessel at the site of a stenosis or aneurysm endoluminally, i.e. by so-called "minimally invasive techniques" in which the endograft, typically restrained in a radially compressed configuration by a sheath, crocheted or knit web, or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to the end outside of the body, whereas the term "distal" is used to refer to portions relatively closer to the end inside the body.

After the introducer is advanced into the body lumen to the endograft deployment location, the introducer is manipulated to cause the endograft to be deployed from its constrained configuration, whereupon the stent is expanded to a predetermined diameter at the deployment location, and the introducer is withdrawn. Stent expansion is typically effected by spring elasticity, balloon expansion, and/or by the self-expansion of a thermally or stress-induced return of a memory material to a pre-conditioned expanded configuration.

Among the many applications for endografts is that of deployment in lumen for repair of an aneurysm, such as an abdominal aortic aneurysm (AAA). An AAA is an area of increased aortic diameter that generally extends from just below the renal arteries to the aortic bifurcation. AAA generally results from deterioration of the arterial wall, causing a decrease in the structural and elastic properties of the artery. In addition to a loss of elasticity, this deterioration also causes a slow and continuous dilation of the lumen.

The standard surgical repair of AAA is an extensive and invasive procedure typically requiring a weeklong hospital stay and an extended recovery period. To avoid the complications of the surgical procedure, practitioners commonly resort to a minimally invasive procedure using endoluminal endograft to reinforce the weakened vessel wall, as mentioned above. At the site of the aneurysm, the practitioner deploys the endograft, anchoring it above and below the aneurysm to relatively healthy tissue. The anchored endograft diverts blood flow away from the weakened arterial wall, minimizing the exposure of the aneurysm to high pressure.

Intraluminal stents for repairing a damaged or diseased artery or to be used in conjunction with a graft for delivery to an area of a body lumen that has been weakened by disease or damaged, such as an aneurysm of the abdominal aorta, are well established in the art of medical science. Intraluminal stents having barbs, hooks, or other affixation means to secure the stents to the wall of the lumen in which they are to be deployed are also well known in the art. Referring now to FIG. 1, there is shown an exemplary embodiment of an endograft 10 comprising a stent 11 having a graft lining 12 and a plurality of hooks 13 for affixation to the wall 14 of aorta 15 afflicted with an aneurysm. The affixation means, such as hooks 13, are important because subsequent movement (or "migration") of the endograft may cause the aneurysm to become exposed to blood pressure. In particular, if the device migrates proximally over time in the direction of arrow A, as shown in FIG. 1, a leak at distal end 16 of the device, sometimes referred to in the art as a "Type I endoleak," may cause blood to flow undesirably to the aneurysm.

Even with standard affixation means, however, continued progression of the aneurysm may lead to diametric expansion of the aneurysm along arrows B as shown in FIG. 1. In particular, in AAA applications, the portion of the aneurysm closest to the renal arteries 17, referred to herein as the "renal neck" 18, may undergo this diametric expansion. The "renal neck" is often referred to by practitioners as the "proximal neck" where the term "proximal" means anatomically as closer to the heart.

Because this application does not use anatomical definitions of "proximal" and "distal," the term "renal neck" is used herein avoid confusion. This diametric expansion of the renal neck may result in ineffective engagement of one or more of the hooks around the circumference of the renal neck, and may lead to a Type I endoleak, as illustrated by separation 20 between aorta wall 14 and endograft 10 in FIG. 2, and/or distal migration of the endograft.

Accordingly, it can be seen that while the art has advanced the use of barbs to minimize migration of a deployed stent-graft, even the use of such barbs may not be sufficient to prevent endoleaks. Accordingly, there is still a need in the art for endograft designs having enhanced affixation characteristics.

SUMMARY OF THE INVENTION

The foregoing general description and subsequent detailed description are representative, not restrictive, of the invention.

One aspect of the invention comprises an endoluminal device for affixation to a wall of a body lumen having a neck region defined by a relatively narrow width and a shoulder region that diverges from the neck region to a relatively wider width. The device comprises a shoulder portion, having a diameter profile that conforms to the shoulder region, such as a shoulder portion having a bulbous geometry, for deployment in the shoulder region. At least part of the shoulder region may further comprise a plurality of affixation members, including but not limited to hooks, barbs, or other members that project radially outward from the device. In one embodiment, the device comprises an endograft comprising a stent that is at least partially covered or lined with a graft material, for example, an endograft adapted to repair an aneurysm such as an AAA. The endoluminal device typically comprises a compressed configuration and a radially expanded configuration, and in at least one embodiment, the device neck has a first radial self-expansion force and the bulbous portion has a second radial self-expansion force less than the first radial expansion force.

Another aspect of the invention comprises an endograft for repair of an AAA. The endograft comprises a stent at least partially lined or covered by a graft material and having enhanced affixation characteristics, the endograft having a first end comprising a distal neck having a first diameter and a shoulder portion located adjacent the distal neck and having a diverging then converging diameter greater than the first diameter. At least the distal neck and part of the shoulder portion may comprise a plurality of affixation members that project radially outward from the device for affixation to the lumen wall of the AAA. The plurality of affixation members are typically disposed in an area of the endograft that extends axially from the distal end of the endograft to at least an intermediate location in the bulbous portion, and in one embodiment, to a maximum diameter portion of the bulbous portion. In one embodiment, the endograft may further comprise a proximal end comprising at least one proximal neck having a second diameter and a second bulbous portion located distally of the proximal neck and having a distally diverging then converging diameter greater than the second diameter, at least the proximal neck and part of the second bulbous portion comprising a plurality of affixation members that project radially outward from the device for affixation to the lumen wall of the AAA.

Yet another aspect of the invention comprises a method for inhibiting diametric expansion of an aneurysm. The method comprises deploying an endograft in the aneurysm, the endograft having an endograft neck with a diameter approximately equal to the width of the aneurysm neck region and a bulbous portion having at least a distal portion adapted to match a proximally diverging width of the shoulder region of the aneurysm, wherein the endograft neck and the distal portion of the bulbous portion comprise a plurality of affixation members for affixing to the lumen wall of the aneurysm.

Still another aspect of the invention comprises a method of inhibiting endoleak formation and migration of an endograft deployed in a lumen, the lumen having a lumen wall, a lumen neck region having a lumen neck width, and a lumen shoulder region proximal the lumen neck region having a proximally diverging width greater than the lumen neck region width. The method comprises providing the endograft with an endograft neck having a diameter approximately equal to the lumen neck region diameter and a shoulder portion adapted to match the proximally diverging diameter of the lumen shoulder region. The method may further comprise providing the endograft neck and the distal portion of the shoulder portion with a plurality of affixation members for affixing to the lumen wall. The shoulder portion may be provided as part of a bulbous portion.

An additional aspect of the invention comprises a method of repairing a body lumen having a lumen wall, a lumen neck region having a lumen neck width, and a lumen shoulder region proximal the lumen neck region having a proximally diverging width greater than the lumen neck region width. The method comprises the steps of providing an endograft having the shoulder portion, bulbous portion and affixation members as described herein and having an expanded configuration and a compressed configuration; constraining the endograft in the compressed configuration for introduction into the body lumen; advancing the endograft to a deployment location aligned with the lumen neck region and lumen shoulder region; and deploying the endograft so that one or more of the affixation members attached to the endograft neck affix to the lumen neck region and one or more of the affixation members attached to the shoulder portion affix to at least a portion of the lumen shoulder region. The method may be used for repairing an aneurysm, such as an AAA. Where the endograft comprises a self-expanding stent having at least a partial covering or lining of a graft material, the method may comprise the stent exerting a radial expansion force against the lumen wall in the neck region that is greater than the radial expansion force exerted by the bulbous portion. Where the endograft comprises a modular device having at least two modular components—a first modular component comprising a distal bulbous region and one or more second modular components each comprising a proximal bulbous region—the method may comprise deploying the first modular component and deploying the one or more second modular components to mate with the first modular component.

BRIEF DESCRIPTION OF THE DRAWING

The invention is best understood when the following detailed description is read with reference to the attached drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
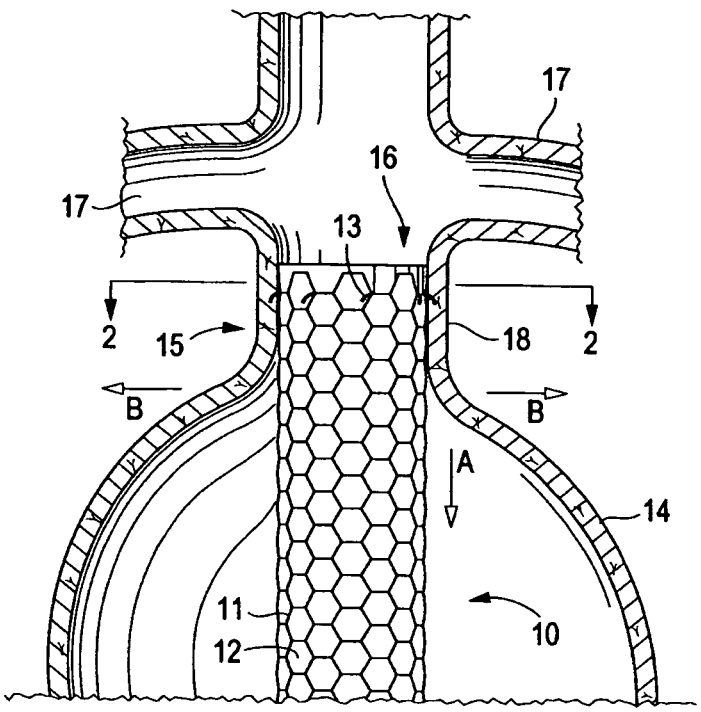
FIG. 1 is an illustration of a cross-section of an abdominal aortic aneurysm (AAA), showing a plan view of an exemplary endograft of the prior art deployed therein.
Figure 2:
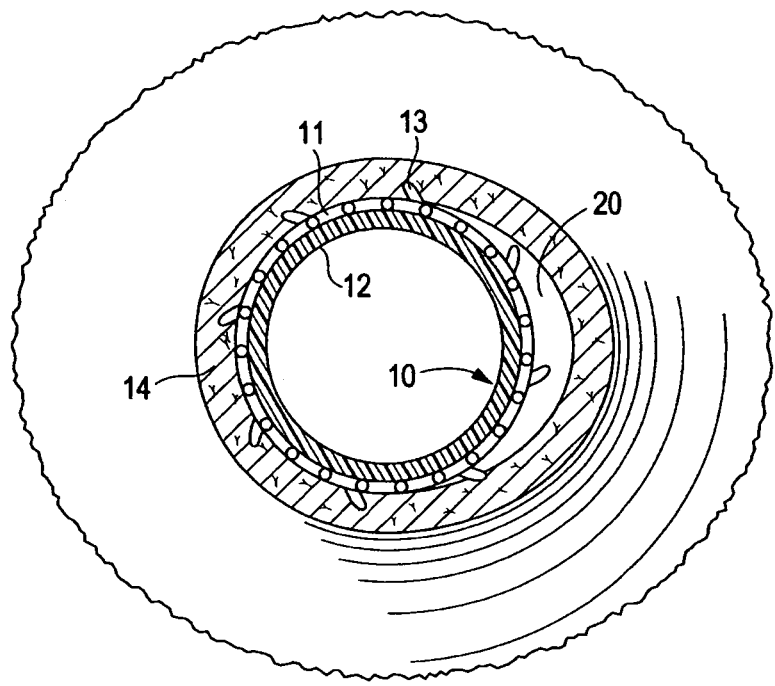
FIG. 2 is a cross-sectional illustration of the endograft and aorta of FIG. 1 taken across line 2-2, illustrating a Type I endoleak.
Figure 3:
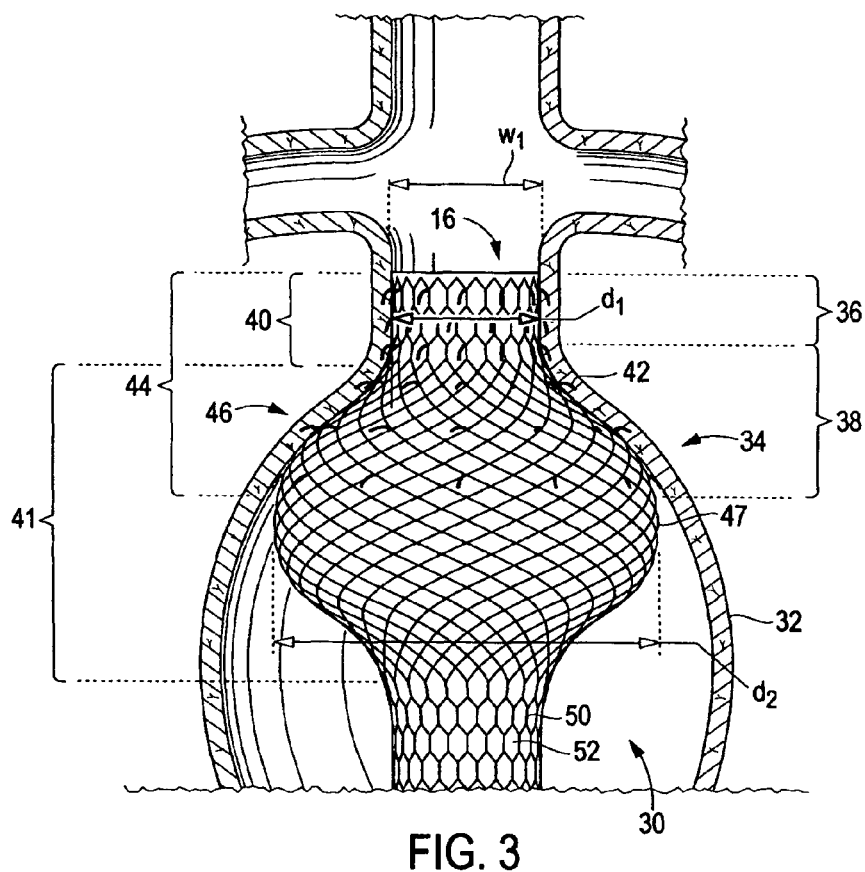
FIG. 3 is a plan view of an exemplary endoluminal device having a distal bulbous portion deployed in renal neck and shoulder region of an AAA shown in cross-section.

Referring now to FIG. 3, there is shown an endoluminal device 30 for affixation to the lumen wall 32 of diseased aorta 34 that is afflicted with an aneurysm. Diseased aorta 34 comprises a neck region 36 defined by a relatively narrow width $w_1$, and a shoulder region 38 that diverges from the neck region to a relatively wider width greater than $w_1$. Device 30 comprises a device neck 40 (also referred to herein as "distal neck" in reference to FIG. 3 and "endograft neck") having a relatively constant diameter $d_1$ along its length and a bulbous portion 41 having a proximally diverging then converging diameter greater than diameter $d_1$ along its length. It should be noted that although the term "diameter" is used herein, the invention is not limited to embodiments having a perfectly circular cross-section. Thus, the term "diameter" should be interpreted to refer to the "effective diameter" of non-circular cross-sections, meaning an average of the width across the device at a given axial plane. At least the distal, shoulder portion 46 of bulbous portion 41 conforms to the contour of shoulder region 38. A plurality of affixation members 42 are disposed throughout an affixation area 44 that spans proximally from the distal or upstream end 16 of the device, through neck 40 and through at least distal portion 46 of bulbous portion, preferably to an intermediate location in the bulbous portion, such as to maximum diameter portion 47 having a diameter $d_2$. The affixation members typically comprise hooks, barbs, other members that project radially outward from the device, or any type of member known in the art for affixing an endoluminal device to a lumen wall.

Endoluminal device 30 as shown in FIG. 3 is an endograft comprising a stent 50 and a graft 52, which is shown in FIG. 3 as a lining on the radial inside surface of the stent. As is well known in the art, the graft material may also be provided as a covering on the radial outside surface of the stent. In some embodiments, the stent may comprise a self-expanding stent as is known in the art. Because of the weakened structure of the diametrically expanded walls of the aneurysm, in some embodiments it may be particularly advantageous for self-expanding stents to exert a lesser radial self-expansion force at bulbous portion 41 than at distal neck 40. This difference in radial self-expansion force between the two areas may be important to minimize the risk of rupture during device placement.

The difference in radial self-expansion force may be provided by providing different stent geometries or stent architectures in the different portions of the stent. Methods of providing different properties in different portions of a stent are described in U.S. patent application Ser. No. 09/442,192 ("the '192 Application"), filed Nov. 16, 1999, titled ENDOLUMINAL STENT HAVING A MATCHED STIFFNESS REGION AND/OR A STIFFNESS GRADIENT AND METHODS FOR PROVIDING STENT KINK RESISTANCE and in U.S. patent application Ser. No. 09/442,165 ("the '165 application"), filed Nov. 16, 1999, titled MULTI-SECTIONAL FILAMENTARY ENDOLUMINAL STENT, both of which are incorporated herein by reference. For example, as detailed in the '192 application, different stent geometries and/or architectures may be used to provide portions having different radial strength, which in turn exert different amounts of radial force. Specifically, a wound stent architecture, such as the hexagonal cell architecture shown in FIG. 3, may be provided in neck 40 and a braided architecture may be provided in bulbous portion 41, in accordance with the hybrid wound/braided stents discussed generally in the '165 application. Exemplary structures and methods for providing affixation members on stents are described in U.S. patent application Ser. No. 10/153,351, filed on May 22, 2002, by James Weldon and Zarouhi Minasian and titled ENDOLUMINAL DEVICE HAVING BARB ASSEMBLY AND METHOD OF USING SAME, incorporated herein by reference. In particular, the '351 application describes structures for providing affixation members for braided portions of hybrid wound/braided stents and at the intersection of a braided portion and a wound portion.

FIG. 3 shows only a distal portion of endograft 30, which may comprise a trunk section of a bifurcated device that has two proximal legs for repairing an abdominal aortic aneurysm (AAA). The invention is not limited, however, to any particular type of device or application. For example, the proximal portion of endograft 30 (not shown) may not branch into any legs, may have more than two legs or branches, may be a modular design comprising one leg and female member for receiving a second leg, or may have any design known in the art. Furthermore, a bulbous portion with affixation members may be provided as part of any type of endoluminal device in addition to use with endografts, such as but not limited to stents without a graft covering or lining, filters, coils, occlusion baskets, valves, and the like. Although endograft 30 is shown repairing an AAA, an endograft having a bulbous portion with affixation members may also be beneficial for repairing a thoracic aortic aneurysm (TAA) or an aneurysm in any location in the body. The use of a bulbous portion with affixation members may also prove beneficial in non-aneurysmal applications having a geometry that can benefit from the bulbous geometry.

Deploying an endograft as described herein in an aneurysm may advantageously inhibit diametric expansion of the aneurysm by radially fixturing the marginally diseased tissue in the shoulder region of the aneurysm. By preventing or at least delaying continued diametric expansion of the shoulder region, the endograft may thereby inhibit progression of the disease and better prevent a rupture of the aneurysm. The increase in length of endograft engagement along the aortic wall also inhibits endoleak formation by providing improved migration resistance and better sealing as compared to endografts lacking the bulbous portion. Furthermore, the increased affixation area provides a longer path for Type 1 endoleaks to travel prior to entering and subsequently repressurizing the aneurysmal sac. The longer pathway thus increases the chance of spontaneous endoleak stagnation and thrombosis which may repair the endoleak without need for surgical intervention or other remedial measures. The logic followed by the present invention is that it is more beneficial to minimize the risk of subsequent aneurysmal rupture than to restore the original cylindrical aortic geometry. The exertion of less radial force by bulbous portion 41 of endograft 30 than by neck 40 is consistent with this logic, because the lesser radial force minimizes the risk that the radial force exerted by the stent itself might rupture the aneurysm.

Figure 4:
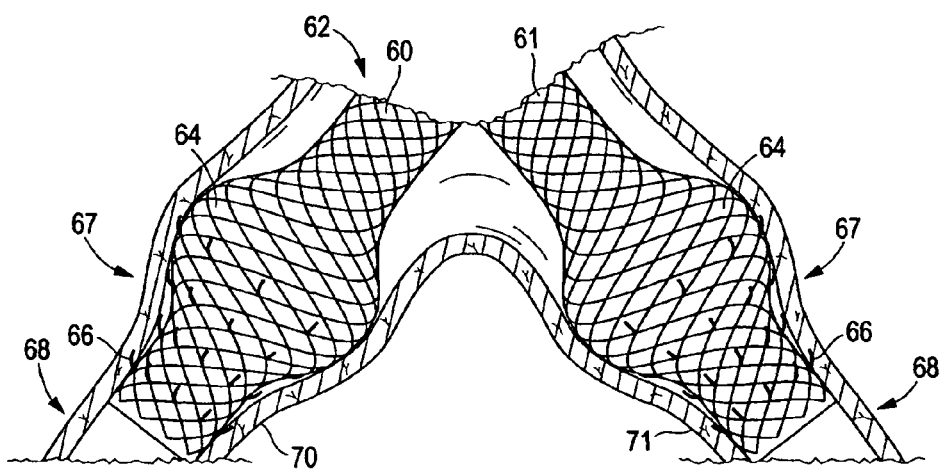
FIG. 4 is a plan view of another exemplary endoluminal device of the present invention comprising a plurality of proximal bulbous portions deployed in the iliac neck and shoulder regions of an AAA shown in cross-section.

The advantages described above with respect to the embodiment shown in FIG. 3 may also be enjoyed in other locations. Referring now to FIG. 4, there is shown another embodiment of the present invention comprising iliac leg portions 60 and 61 of an endograft 62, each having proximal bulbous portions 64 and a plurality of affixation members 66. Bulbous portions 64 are adapted for deployment in shoulder regions 67 located distally of iliac necks 68 of iliac arteries 70 and 71 at the proximal end of an aneurysm. Like the embodiment shown in FIG. 3, the use of such an embodiment may prevent or delay continued diametric expansion of shoulder region 67, thereby inhibiting progression of aneurysmal disease, and may also inhibit endoleak formation by providing improved migration resistance and better sealing as compared to endografts lacking the bulbous portion.

Leg portions 60 and 61 may be part of a modular or non-modular AAA prosthesis comprising a distal bulbous portion 41 as depicted in FIG. 3, or may be part of a modular or non-modular AAA prosthesis comprising a standard, non-bulbous trunk portion known in the art. The connections between leg portions 60 and 61 and prosthesis 30 may comprise any connection for modular or non-modular prostheses known in the art, including embodiments in which distal bulbous portion 41 and one of proximal bulbous portions leg portions 60 and 61 are part of a single modular component, and the other leg comprises a mating modular component. Embodiments in which both leg portions are modular components or both legs are integral components may also be provided. Leg portions 60 and 61 may be deployed by any method known in the art.

Although depicted as two leg members 60 and 61 for deployment in iliac arteries 70 and 71, respectively, it should be understood that a prosthesis may comprise more than two dependent members of any type, and that such a prosthesis having dependent members may be adapted for deployment in any type of body lumen. Furthermore, although both leg members are shown with bulbous portions in FIG. 4, embodiments may also be provided in which less than all of the multiple dependent members have bulbous portions.

Figure 5:
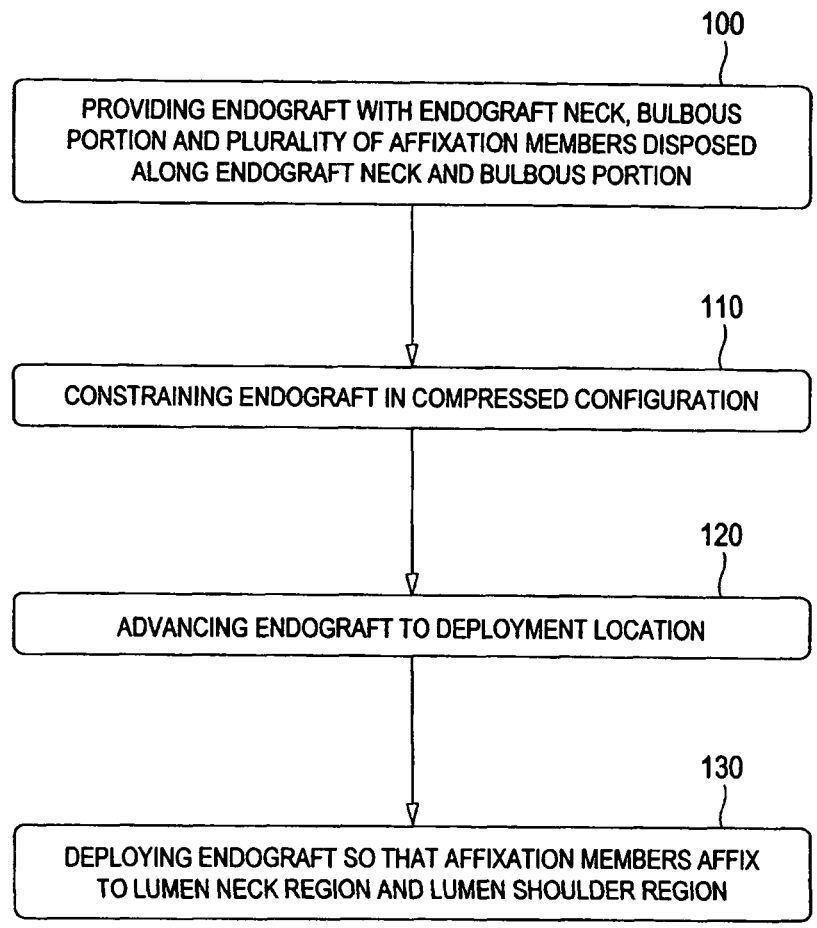
FIG. 5 is a flowchart depicting an exemplary method of the invention.

Thus, the endograft embodiments of the present invention may be used for performing a method of repairing a body lumen, as depicted in the flowchart shown in FIG. 5. The method first comprises step 100 of providing an endograft having an expanded configuration as shown in FIG. 3 and a compressed configuration (not shown), similar to the compressed configuration known in the art for any endoluminal device. In the expanded configuration, the endograft has a neck 40 with diameter $d_1$ approximately equal to the lumen neck region width $w_1$ and a bulbous portion 41 having at least a distal, shoulder portion 46 adapted to match the diverging width of lumen shoulder region 38. Endograft 30 comprises a plurality of affixation members 42 for affixing to lumen wall 32, the affixation members disposed along an axial portion 44 of endograft 30 including at least neck 40 and distal portion 46 of bulbous portion 41. The method then comprises step 110 of constraining the endograft in its compressed configuration for introduction into the body lumen. Next, in step 120, the compressed and constrained endograft 30 is advanced to a deployment location aligned with the lumen neck region and lumen shoulder region, such as the region shown in FIG. 3. Finally, in step 130, endograft 30 is deployed so that one or more of affixation members 42 in endograft neck 40 affix to lumen neck region 36 and one or more of the affixation members in bulbous portion 41 affix to at least a portion of lumen shoulder region 38. As shown in FIG. 3, where stent 50 is a self-expanding stent, the stent in the area of neck 40 exerts a radial expansion force that is greater than the radial expansion force exerted in the area of bulbous portion 41.

For a modular endograft with multiple bulbous regions, such as an endograft comprising bulbous portion 41 at its distal end, as shown in FIG. 3, and iliac leg portions 60 and 61 at its proximal end, as shown in FIG. 4, it may be desirable to first deploy bulbous portion 41 as described above, and then reverse-deploy the leg portions to assure desired placement of the bulbous portions 64. Exemplary reverse deployment methods are described generally in U.S. application Ser. No. 10/080,791, filed Feb. 22, 2002, by Haverkost et al., titled METHOD AND SYSTEM FOR DEPLOYING MULTI-PART ENDOLUMINAL DEVICES, incorporated herein by reference.

The devices as well as any graft linings or coatings used with the devices of the present invention may comprise any suitable materials of construction known in the art, including any type of surface modification known in the art. For example, it may be desirable to provide the device with a coating of a biologically or pharmacologically active substance for enhancing the effectiveness of the device generally, or of the shoulder or bulbous portion specifically. The term "biologically or pharmacologically active substance" refers to any substance, whether synthetic or natural, that has a pharmacological, chemical, or biological effect on the body or a portion thereof. Suitable biologically or pharmacologically active materials that can be used in this invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine and doxazosin. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

Additional biologically or pharmacologically active substances and carriers for these substances are listed in U.S. Pat. No. 6,364,856; No. 6,358,556; and No. 6,258,121; all of which are incorporated herein by reference. In addition to disclosing additional active substances, these patent references disclose polymer materials impregnated with active substances for use as coatings on the outside of medical devices to provide controlled delivery of the active substances. Devices of the present invention may also comprise such impregnated polymer materials.

Although the aorta illustrated in FIG. 3 has a generally regular shape, aneurysms with irregular shapes are not uncommon. Therefore, it may be additionally desirable to provide the device with one or more portions, particularly the shoulder or bulbous portion, with the ability to conform to an irregular shape. This may be accomplished using a balloon-expandable stent framework having plastically-deformable materials of construction, such as but not limited to gold, platinum, tantalum, titanium, stainless steel, tungsten, a cobalt alloy, a nickel or titanium alloy, such as a plastically deformable grade of nitinol or deformable core nitinol composite, or a combination of any of the above. A combination self-expanding, balloon-expandable stent framework may also be used, comprising a combination of superelastic and plastically deformable materials, such as is described, for example, in U.S. patent application Ser. No. 09/702,226, to Steven E. Walak, titled COMBINATION SELF-EXPANDABLE, BALLOON-EXPANDABLE ENDOLUMINAL DEVICE, filed Oct. 31, 2000, and incorporated herein by reference. Methods of using such devices include deploying the device initially by self-expansion, followed by modeling the plastically deformable sections to conform to the lumen geometry using an inflatable balloon or other modeling device Although the bulbous portions disclosed in the present invention are shown at or near the ends of the devices, it should be understood that a bulbous portion may be provided at any location on a device. Furthermore, although a bulbous configuration has been generally described herein, it should be understood that the important characteristic of the device is that the shoulder portion have a diameter profile that conforms to the contour of the shoulder region of the lumen. By "diameter profile that conforms to the contour" it is meant that if the lumen shoulder region diameter diverges from a neck region having a first diameter to a relatively wider second diameter along a given length with a given slope, the shoulder portion of the device similarly diverges from approximately the first diameter to approximately the second diameter along approximately the same given length with approximately the same given slope. Thus, if lines plotting the diameter versus length were graphed for the shoulder region of the device and the shoulder region of the lumen, the line corresponding to the shoulder portion of the device would have a similar slope the line for the shoulder region of the lumen. While it is important that shoulder portion 46 of device 30 shown in FIG. 3 has a configuration that conforms to shoulder region 38 of the lumen, the device proximal of shoulder portion may have any configuration, such as a configuration with a tapering diameter or even a step-change back to diameter $d_1$ rather than the bulbous configuration shown.

Finally, providing a bulbous portion or other defined shoulder portion having a diameter profile that conforms to the contour of the shoulder region of the lumen in which the device is implanted is advantageous both by itself and in conjunction with providing affixation members in the bulbous or shoulder portion. Although the figures shown herein depict bulbous or shoulder portions with affixation members, it should be recognized that devices having such portions without affixation members may also be provided.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. In particular, for example, although some embodiments have been described herein having elements labeled with "distal" or "proximal" directional descriptors, it should be understood that one equivalent embodiment may comprise the same elements with the directional descriptors reversed.

What is claimed is:

1. A self-expanding endoluminal device having a compressed configuration and a self-expanded configuration, the device in the self-expanded configuration comprising a first neck, a bulbous portion defining a convex exterior surface, a second neck, a first shoulder portion located between the first neck and the bulbous portion and defining a concave exterior surface therebetween, and a second shoulder portion located between the second neck and the bulbous portion and defining a concave exterior surface therebetween, the first neck having a first diameter, the bulbous portion having a geometry characterized by a diverging and converging diameter greater than the first diameter, the diverging and converging diameter forming the first and second shoulder portions, respectively, wherein the first neck is configured in a polygonally wound stent architecture to exert a first radial self-expansion force applied to a lumen wall and the bulbous portion is configured in a braided stent architecture to exert a second radial self-expansion force applied to the lumen wall in a shoulder region that is less than the first radial expansion force.

2. The device of claim 1, wherein the bulbous portion of the device comprises a stent having at least one superelastic section and at least one plastically deformable section.

3. The device of claim 1 further comprising a plurality of affixation members at least on part of the device shoulder portion.

4. The endoluminal device of claim 3, wherein the affixation members comprise hooks, barbs, or other members that project radially outward from the device.

5. The endoluminal device of claim 3, wherein the device has a distal end adapted to be positioned in an upstream portion of a lumen and the plurality of affixation members are disposed in an area of the device extending proximally from the distal end of the device through the first shoulder portion.

6. The endoluminal device of claim 5, wherein an area in which the plurality of affixation members are disposed extends axially to a maximum diameter portion of the first shoulder portion.

7. The endoluminal device of claim 1, wherein the device comprises a stent.

8. The device of claim 7, wherein the stent comprises at least one superelastic section and at least one plastically deformable section.

9. The device of claim 1, wherein the first shoulder portion of the device comprises a stent having at least one superelastic section and at least one plastically deformable section.

10. The endoluminal device of claim 1, wherein the first neck portion includes a renal neck portion adapted to be positioned at a distal end of an aneurysm and the first device shoulder portion is adapted to be positioned proximal a renal neck at the lumen shoulder region.

11. The endoluminal device of claim 1, wherein the first neck portion includes an iliac neck portion adapted to be positioned at a proximal end of an aneurysm and the first device shoulder portion is adapted to be positioned distally of the iliac neck.

12. The endograft of claim 1, wherein the plurality of affixation members are disposed in an area that extends axially from a distal end of the endograft to at least an intermediate location in the first bulbous portion.

13. The device of claim 1, wherein the device converging diameter length comprises a tapered or step-change diameter.

14. The endoluminal device of claim 1, wherein the device comprises an endograft comprising a stent that is at least partially covered or lined with a graft material.

15. The endoluminal device of claim 14, wherein the endograft is adapted to repair an aneurysm.

16. The endoluminal device of claim 15, wherein the endograft is adapted to repair an abdominal aortic aneurysm (AAA).

17. A self-expanding endoluminal device having a compressed configuration and a self-expanded configuration and having a distal end, the device in the self-expanded configuration comprising a distal first neck, a first bulbous portion defining a convex exterior surface, a distal second neck, a first shoulder portion located between the distal first neck and the first bulbous portion and defining a concave exterior surface therebetween, and a second shoulder portion located between the distal second neck and the first bulbous portion and defining a concave exterior surface therebetween, the distal first neck having a first diameter, the first bulbous portion having geometry characterized by a diverging and converging diameter greater than the first diameter, the diverging and converging diameter forming the first and second shoulder portions, respectively, at least the distal first neck and part of the first bulbous portion comprising a plurality of affixation members that project radially outward for affixation to a lumen wall of an abdominal aortic aneurysm, wherein the distal first neck is configured in a polygonally wound stent architecture to exert a first radial self-expansion force applied to the lumen wall and the bulbous portion is configured in a braided stent architecture to exert a second radial self-expansion force applied to the lumen wall in a shoulder region that is less than the first radial expansion force.

18. The device of claim 17, wherein the area in which the plurality of affixation members are disposed extends axially to a maximum diameter portion of the first bulbous portion.

19. The device of claim 17 further comprising a proximal end comprising at least one proximal neck having a second diameter and an additional corresponding bulbous portion located distally of the proximal neck and having a distally diverging then converging diameter greater than the second diameter, at least the proximal neck and part of the additional corresponding bulbous portion comprising a plurality of affixation members that project radially outward from the device for affixation to the lumen wall of the abdominal aortic aneurysm.

20. The device of claim 19 further comprising a plurality of affixation members at least on part of the device first distal shoulder portion and on part of the device proximal shoulder portion.

21. The endoluminal device of claim 19, wherein the device first distal shoulder portion and the device proximal shoulder portion comprises a non-modular device.

22. The endoluminal device of claim 19, wherein the device distal shoulder portion and the device proximal shoulder portion comprises a modular device.

23. The endoluminal device of claim 22, wherein a first modular component comprises the device first distal shoulder portion and a first device proximal shoulder portion, and a second modular component comprises a second device proximal shoulder portion.

24. The device of claim 19 comprising two proximal necks and two additional corresponding bulbous portions, each proximal neck and additional corresponding bulbous portion for deployment adjacent an iliac neck region of the abdominal aortic aneurysm.

25. The device of claim 24, wherein the distal first and second necks, first bulbous portion and first and second shoulder portions comprise a first modular component, and each proximal neck and additional corresponding bulbous portion comprise additional modular components.

26. The device of claim 24, wherein the distal first and second necks, first bulbous portion, first and second shoulder portions, one proximal neck, and one additional corresponding bulbous portion comprise a first modular component, and another proximal neck and additional corresponding bulbous portion comprise a second modular component.

27. The device of claim 17 wherein the device comprises a stent at least partially lined or covered by a graft material.

28. The endoluminal device of claim 27, wherein the endograft is adapted to repair the abdominal aortic aneurysm.

29. The endoluminal device of claim 17, wherein the endograft is adapted to repair an aneurysm.

* * * * *